(12) United States Patent
Orvig et al.

(10) Patent No.: US 6,287,586 B1
(45) Date of Patent: Sep. 11, 2001

(54) PHARMACEUTICAL COMPOSITIONS OF VANADIUM BIGUANIDE COMPLEXES AND THEIR USE

(75) Inventors: Chris Orvig, Vancover; John H. McNeill, Vancouver, both of (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 09/396,982

(22) Filed: Sep. 15, 1999

Related U.S. Application Data
(60) Provisional application No. 60/101,074, filed on Sep. 18, 1998.

(51) Int. Cl.[7] .............................. A61K 9/10; A61K 31/28

(52) U.S. Cl. .......................... 424/423; 514/184; 514/866

(58) Field of Search .................................. 514/184, 866; 424/464, 451, 489, 499, 423, 436, 45

(56) References Cited

U.S. PATENT DOCUMENTS

| | | | |
|---|---|---|---|
| 5,188,833 | * 2/1993 | Kamijo et al. | 424/405 |
| 5,300,496 | 4/1994 | McNeill et al. | 514/184 |
| 5,527,790 | 6/1996 | McNeill et al. | 514/186 |
| 5,620,967 | 4/1997 | McNeill et al. | 514/186 |

FOREIGN PATENT DOCUMENTS

93/06811   4/1993  (WO).

OTHER PUBLICATIONS

Babykutty et al. (1974), "Thermal Decomposition of the Biguanide Complexes of the 3d–Transition Metals," *Thermochimica Acta*, vol. 8:271–282.

Chakraborty et al. (1989), "Indirect Determination of Vanadium by Atomic Absorption Spectrometry," *Analytica Chimica Acta*, vol. 218:341–344.

McNeill et al. (1985), "Effect of Vanadate on Elevated Blood Glucose and Depressed Cardiac Performance of Diabetic Rats," *Science*, vol. 227:1474–1477.

Pederson et al. (Nov. 1989), "Long–Term Effects of Vanadyl Treatment on Streptozocin–Induced Diabetes in Rats," *Diabetes*, vol. 38:1390–1395.

Ramanadham et al. (1989), "Oral Vanadyl Sulfate in Treatment of Diabetes Mellitus in Rats," *Am. J. Physiol.*, vol. 257:H904–H911.

Ramanadham et al. (Oct. 1989), "Sustained Prevention of Myocardial and Metabolic Abnormalities in Diabetic Rats Following Withdrawal from Oral Vanadyl Treatment," *Metabolism*, vol. 38(10):1022–1028.

Ramanadham et al. (1990), "Enhanced in Vivo Sensitivity of Vanadyl–Treated Diabetic Rats to Insulin," *Can J. Physiol. and Pharmacol.*, vol. 68:486–491.

Ray (1961), "Complex Compounds of Biguanides and Guanylureas with Metallic Elements," *Chem Rev.*, vol. 61:313–359.

(List continued on next page.)

*Primary Examiner*—Edward J. Webman
*Assistant Examiner*—Helen Nguyen
(74) *Attorney, Agent, or Firm*—Pamela J. Sherwood; Bozicevic, Field & Francis LLP

(57) ABSTRACT

Pharmaceutical compositions of vanadium biguanide complexes, and methods of use, are provided for the treatment of hyperglycemia and related disorders, e.g. hypertension, obesity, and lipid disturbances. The pharmaceutically active complexes of the invention comprise a biguanide chelant, preferably a 1-substituted biguanide chelant, capable of chelating vanadium to form a six-membered unsaturated vanadium-containing ring. The vanadium of the complex is coordinated with oxygen, sulphur or nitrogen, particularly oxygen coordinated. The complexes are formulated with a physiologically acceptable carrier. In a preferred embodiment, the complexes are formulated for oral administration.

10 Claims, 1 Drawing Sheet

OTHER PUBLICATIONS

Sakurai et al. (Sep. 1980), "Detection of Oxovanadium (IV) and Characterization of its Ligand Environment in Subcellular Fractions of the Liver of Rats Treated with Pentavalent Vanadium (V)," *Biochem. and Biophys. Res. Comm.*, vol. 96(1):293–298.

Shechter et al. (Apr. 1980), "Insulin–Like Stimulation of Glucose Oxidation in Rat Adipocytes by Vanadyl (IV) Ions," *Nature*, vol. 284:556–558.

Syamal (1983), *Ind. J. Pure and Applied Phys.*, vol. 21:130–132.

Babykutty, P.V., et al., "Electronic and Infrared Spectra of Biguanide Complexes of the 3d–Transition Metals," *Journal of Inorganic & Nuclear Chemistry* (1974) vol. 36(12):3685–3688.

Elpern, Bill, "Chemistry of the Biguanides," *Annals of the New York Academy of Sciences* (Mar. 26, 1968) vol. 148(3):577–586.

McNeill, "Bis(maltolato)oxovanadium(IV) is a Potent Insulin Mimic," *Journal of Medicinal Chemistry, US, American Chemical Society*, Washington (Apr. 17, 1992) vol. 35(8):1489–1491.

Ramasarma, T., "Vanadium Complexes With Insulin Mimic Actions–A Second Line of Protection Against Diabetes," *Indian Journal of Clinical Biochemistry* (1996) vol. 11(2):92–107.

Scheen, André J., "Drug Treatment of Non–Insulin–Dependent Diabetes Mellitus in the 1990s," *Drugs, AT, ADIS International Ltd.*, (Sep. 1, 1997) vol. 53(3):355–368.

Vialettes, B., et al., "Pharmacological Approach in the Treatment of Insulin Resistance," *Horm Res* (1992) vol. 38:51–56.

Calatayud et al. (Nov./Dec. 1981), "Estudio de la Reactividad del Clorhidrato de Fenilbiguanida con los Iones," *Afinidad*, vol. 28:537–540 (in Spanish).

* cited by examiner

PHARMACEUTICAL COMPOSITIONS OF VANADIUM BIGUANIDE COMPLEXES AND THEIR USE

This application claims priority to provisional application No. 60/101,074, filed on Sep. 18, 1998.

BACKGROUND OF THE INVENTION

Non-insulin-dependent diabetes mellitus (NIDDM) is a metabolic disease that affects about 5% to 7% of the population in western countries (and 10% of individuals over age 70). It is characterized by hyperglycemia and often accompanied by a number of other conditions, including hypertension, obesity and lipid disturbances. The underlying pathology is impaired beta-cell function of uncertain cause. Insulin resistance, which both precedes and predicts impaired glucose tolerance, may be the cause of beta-cell failure, or it may simply reveal the presence of a primary beta-cell defect.

Diet and exercise therapy alone are generally not successful in controlling hyperglycemia in NIDDM. In contrast to IDDM, in which insulin deficiency is the problem and insulin replacement the treatment, in NIDDM the pharmacological approach to hyperglycemia is more varied and more rapidly evolving. The data suggest that any improvement in the degree of blood glucose control will postpone development and slow the progression of microvascular complications. Treatment goals for people with diabetes that emphasize glycemic control are therefore recommended.

There are four classes of currently approved antidiabetic drugs in the United States, each of which have different effects on one or more of the pathogenetic abnormalities of NIDDM. The sulfonylurea agents all appear to act primarily by potentiating insulin secretion. In contrast, the biguanides have no direct effect on insulin secretion. Their mechanism or mechanisms of action are not completely understood but include a reduction in hepatic glucose production and perhaps an increase in peripheral insulin sensitivity and reduction in intestinal glucose absorption. A third class of drugs is the α-glucosidase inhibitors, which inhibit specific enzymes that break down starches in the small intestine, thereby delaying carbohydrate absorption and attenuating postprandial hyperglycemia. A fourth class of therapeutic drugs is the insulin preparations that supplement endogenous insulin.

Biguanides lower blood glucose primarily by reducing intestinal glucose absorption and hepatic glucose production. Metformin, (1,1-dimethylbiguanide) is rapidly absorbed and cleared through the kidneys. The drug has been shown to reduce fasting and postprandial blood glucose by an average of 2 to 3 mmol/L. It may also enhance insulin sensitivity at postreceptor levels and stimulate insulin-mediated glucose disposal, but it does not stimulate insulin secretion.

The number of patients who respond to biguanide therapy diminishes over the years because of a number of factors, e.g. drug noncompliance because of side effects, dietary noncompliance, weight gain, declining beta-cell function, and the increasing use of diabetogenic drugs such as glucocorticoids, thiazides, and beta-blockers. Metformin is contraindicated in patients with renal dysfunction or conditions that compromise renal function. The drug is also contraindicated in acute or chronic metabolic acidosis.

Compositions that are effective in treating non-insulin dependent diabetes, such as improved biguanide compositions, are of great interest. The invention described herein provides for such improved compositions and methods for their use.

Relevant Literature

Complexes formed between vanadium and biguanides have been described by Chakraborty and Das (1989) *Analytica Chimica Acta* 218:341–344; Syamal (1983) *Ind. J. Pure & Applied Phys.* 21:130–132; Calatayud et al. (1981) *Afinidad* XXXVIII:537–540; Babykutty et al. (1974) *Thermochimica Acta* 8:271–282. A complex of vanadium and 1,1-dimethylbiguanide is disclosed by Ray (1961) *Chem. Rev.* 61:313–359.

The insulin-like effect of the vanadate ion ($VO_4^{3-}$) in vitro has been known since 1980, see Nature 284:556–558 (1980), when it was shown that the insulin-like stimulation of glucose oxidation in rat adipocytes was due to the vanadyl ion. In 1985, McNeill et al. (1985) Science 227: 1474–1477, reported that vanadate, when administered in drinking water, decreased the elevated blood glucose and prevented the depression of cardiac performance in rats made diabetic with streptozotocin (STZ). Subsequently, there has been interest in the insulin-mimetic effects of both vanadate and vanadyl, since Sakurai et al. (1980) Biochem. Biophys. Res. Comm. 96: 293–298, showed that vanadate is reduced in vivo to vanadyl.

Work by McNeill et al. (see Am. J. Physiol 257: H904–H911 (1989), Metabolism 38: 1022–1028 (1985), Diabetes 38: 1390–1395 (1989) and Can. J. Physiol & Pharmacol. 68: 486–491 (1990); U.S. Pat. Nos. 5,527,790; 5,300,496; has shown that vanadyl administered orally as vanadyl sulfate, or as vanadyl maltol complexes lowers blood glucose and blood lipids in STZ diabetic rats and prevents secondary complications of diabetes such as cataracts and cardiac dysfunction.

SUMMARY OF THE INVENTION

Pharmaceutical compositions of vanadium biguanide complexes, and methods of use, are provided for the treatment of hyperglycemia and related disorders, e.g. hypertension, obesity, and lipid disturbances. The pharmaceutical compositions also find use in the treatment of hyperproliferative disorders. The pharmaceutically active complexes of the invention comprise a biguanide chelant, preferably a 1-substituted biguanide chelant, capable of chelating vanadium to form a six-membered unsaturated vanadium-containing ring. The vanadium of the complex is coordinated with oxygen, sulphur or nitrogen, particularly oxygen coordinated. The complexes are formulated with a physiologically acceptable carrier. In a preferred embodiment, the complexes are formulated for oral administration.

DESCRIPTION OF THE SPECIFIC EMBODIMENTS

Figure 1A:
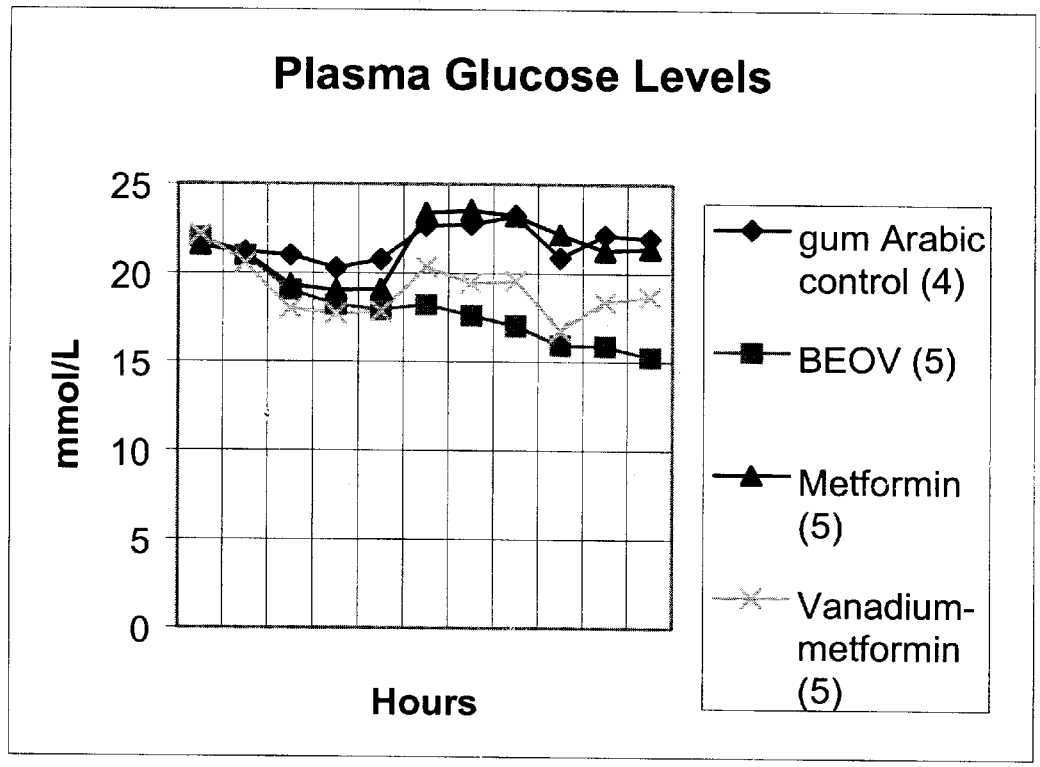
FIG. 1A shows a comparison of the glucose lowering ability of vanadium complexes in diabetic rats over a time course.
Figure 1B:
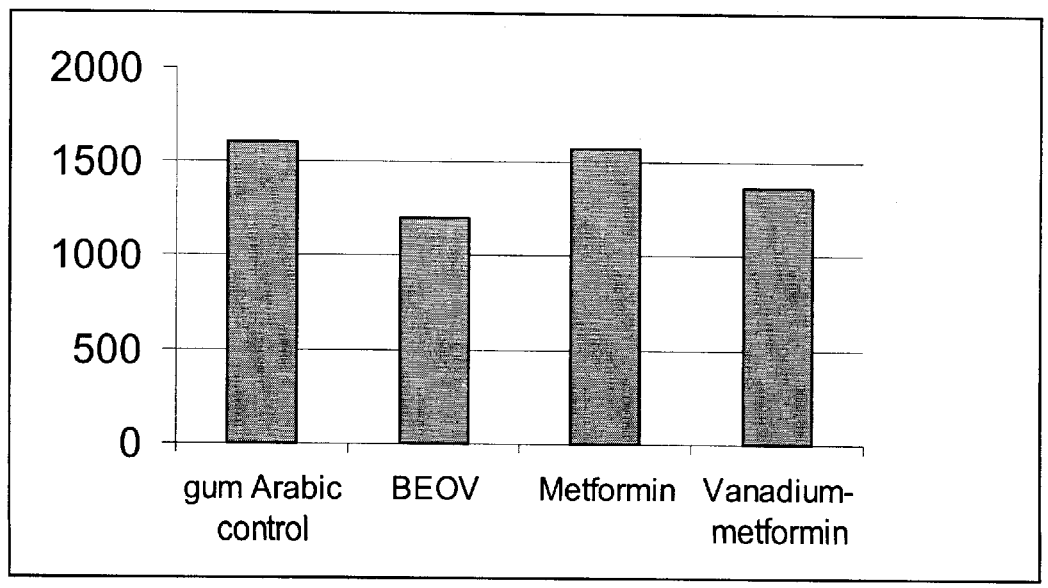
FIG. 1B provides a summary of the comparison, showing the area under the curve (AUC).

Method are provided for the use of vanadium biguanide complexes to treat hyperglycemia, e.g. non-insulin dependent diabetes, and related disorders, which may include, but are not limited to, elevated blood pressure, i.e. hypertension, obesity, lipid disturbances, e.g. hypercholesterolaemia, hypertriglyceridaemia, and the like; and hyperproliferative disorders, e.g. cancer, restenosis, arthritis, and the like. The complexes are formulated with a physiologically acceptable carrier for administration to a patient.

Vanadium Biguanide Complexes

The pharmaceutically active complexes of the invention comprise a biguanide chelant, preferably a 1-substituted biguanide chelant, capable of chelating vanadium to form a six-membered unsaturated vanadium-containing ring. The vanadium of the complex is coordinated with oxygen, sulphur or nitrogen, particularly oxygen coordinated.

In a preferred embodiment, the complexes of the invention have the structure as follows:

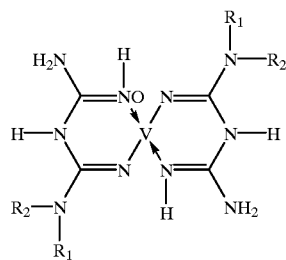

where $R_1$ and $R_2$ are, independently, H; lower alkyls, e.g. methyl, ethyl, propyl, isopropyl, butyl; cycloalkyls, e.g. cyclohexane; aryls, e.g. phenyl, phenethyl, and the like.

Specific chelants of interest have antidiabetic activity apart from their association with vanadium, and may include 1,1-dimethylbiguanide (metformin), 1-phenethylbiguanide (phenformin); and 1-butylbiguanide (buformin).

The vanadium complex used according to the invention is preferably a complex of vanadium(III), (IV) or (V), especially (IV) or (V), with a ligand as described above, especially preferably a complex $VL_3$, $VOL_2$, $VO_2L_2$ or $VOL_2(OR_3)$ where L is a chelant as described above and $R_3$ is an optionally substituted alkyl, aryl, aralkyl or alkenyl group (where such groups are as defined above), preferably such a group is substituted by at least one hydroxyl group.

Vanadium complex formation may be effected by conventional metallation or transmetallation techniques, e.g. by mixture in solution of a soluble vanadium salt with the chelant or a salt or weaker complex thereof.

The invention provides the use of a physiologically tolerable vanadium biguanide complex for the manufacture of an agent useful in lowering elevated blood sugar, as an antihypertensive or blood pressure lowering agent, as an appetite suppressant, and as an agent for regulating hypercholesterolaemia, hypertriglyceridaemia, and other lipid disorders.

Pharmaceutical Formulations

The vanadium complexes can be given by various conventional administration routes, e.g. oral, rectal, intravenous, subcutaneous, intraperitoneal, transdermal, etc. However oral administration is preferred.

Formulations of the vanadium biguanide complexes are administered to a host affected by hyperglycemia, particularly non-insulin dependent diabetes mellitus (NIDDM); by related disorders, which may include obesity, hypertension, hypercholesterolemia, hypertriglyceridemia, and the like; or by diseases related to hyperproliferation of cells. The compounds of the present invention are administered at a dosage that reduces blood sugar, blood pressure, and the like, while minimizing any side-effects. It is contemplated that the composition will be obtained and used under the guidance of a physician for in vivo use. Such guidance may include non-pharmacological pharmacological disease management, e.g. diet, exercise, and the like.

Various methods for administration may be employed. The formulation may be given orally, by inhalation, or may be injected, e.g. intravascular, intratumor, subcutaneous, intraperitoneal, intramuscular, and the like. The dosage of the therapeutic formulation will vary widely, depending upon the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, and the like to maintain an effective dosage level. In many cases, oral administration will require a higher dose than if administered intravenously.

The compounds of this invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, and the like. The complexes may be systemic after administration or may be localized by the use of an implant that acts to retain the active dose at the site of implantation.

In pharmaceutical dosage forms, the compounds may be administered in the form of their pharmaceutically acceptable salts, or they may also be used alone or in appropriate association, as well as in combination with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing vanadium biguanide complexes is placed in proximity to the site of action, so that the local concentration of active agent is increased relative to the rest of the body.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular complex employed and the effect to be achieved, and the pharmacodynamics associated with each complex in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The compositions of the invention may also contain other therapeutically active agents, e.g. antidiabetic, antihypertensive and appetite suppressing agents, e.g. aldose reductase inhibitors, sulfonylureas, $MgCl_2$, chromium picolinate, and the like. Of particular interest are combinations with other agents capable of lowering blood sugar, preferably those which increase the level of insulin in the blood, either as exogenous insulin or by increasing endogenous insulin secretion.

Such agents include benzenesulfonylurea derivatives of the type $R_4C_6H_4SO_2NHCONHR_5$, e.g. acetohexamide at a dose from about 250 mg/day to about 1.5 mg per day, chlorpropamide at a dose from about 100 to 500 mg/day, glipizide at a dose from about 5 to 40 mg per day, glyburide at a dose from about 1 to 20 mg per day, tolazamide at a dose from about 100 to 500 mg per day, and tolbutamide at a dose from about 500 mg to 3 g per day, and the like. In the subject combined therapies the lower dosage levels may be preferred.

Insulin may be administered during the course of treatment with the subject vanadium biguanide complexes. Various compositions and formulations of insulin are known in the art, including recombinant human insulin, bovine or porcine insulin, and the like, as a protamine zinc suspension, zinc suspension, and the like, formulated for intravenous injection, subcutaneous injection, aerosol administration, and the like. Standard adult doses for insulin range from about 5 to 20, and as much as about 80 USP units per day.

The combined used of vanadium biguanide complexes and other antidiabetic agents has the advantages that the required dosages for the individual drugs may be lower, and the onset and duration of effect of the different drugs complementary. In the combined therapy, the different active agents can be delivered together or separately, and simultaneously or at different times within the day. Moreover the compounds may be administered by any convenient and effective route, e.g. by injection, orally, rectally or transdermally. Preferably, where the agents are orally active, administration will be orally and the different agents will be administered substantially simultaneously, preferably as a composition containing both agents. Where one of the agents is insulin, which is not orally active, the agents will generally be separately formulated.

Dosages

Depending on the patient and condition being treated and on the administration route, the vanadium biguanide complexes will generally be administered in dosages of 0.1 mg to 500 mg V/kg body weight per day. The range is broad since in general the efficacy of a therapeutic effect for different mammals varies widely with doses typically being 20, 30 or even 40 times smaller (per unit body weight) in man than in the rat. Similarly the mode of administration can have a large effect on dosage. Thus for example oral dosages in the rat may be ten times the injection dose. As a result, the preferred range for rats is 0.1 to 300 mg Vkg/day while for man it may be 0.007 to 2.0 mg V/kg/day. A typical adult dosage may be 500 milligrams two times a day taken with the meals, 850 mg once a day. The bioavailability of metformin is 50–60%. Food decreases the extent and slightly delays the absorption of metformin, however, it is recommended to be taken with meals. Metformin does not bind to liver or plasma proteins. It is not metabolized by the liver. Metformin is excreted by the kidneys, largely unchanged, through an active tubular process. Approximately 30% of an oral dose is excreted in the feces, presumably as unabsorbed metformin and about 90% of a dose is excreted by the kidneys within 24 hours. The plasma half-life is $_2$6.2 hours and the blood half-life is $_2$17.6 hours in patients with normal renal function. Half-life is increased in patients with renal impairment. Metformin is removed with hemodialysis.

A typical dosage may be one tablet taken from two to three times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

Methods of Use

Patients suitable for the subject therapy include those with non-insulin dependent diabetes mellitus, a mammalian condition in which the amount of glucose in the blood plasma is abnormally high. This condition can be life-threatening and high glucose levels in the blood plasma (hyperglycemia) can lead to a number of chronic diabetes syndromes, for example, atherosclerosis, microangiopathy, kidney disorders, renal failure, cardiac disease, diabetic retinopathy and other ocular disorders including blindness. In diabetics, insulin is not produced in sufficient quantities, or the body becomes tolerant to insulin and requires more than normal amounts to produce the necessary effect.

Patients are generally categorized as diabetic or hyperglycemic by measuring the level of glucose in the blood, either directly or by monitoring the level of glycosylated hemoglobin. Treatment is recommended where fasting glucose levels are greater 140 mg/dl, where bedtime glucose is greater than 160 mg/dl, or where $HbA_{1c}$ is greater than 8%. The level of reduction that is desirable depends on the condition of the patient, and the blood glucose levels at the start of treatment, but generally about a 10 to 40 % reduction is blood glucose is desirable, usually about a 25 to 35% reduction.

Glycemic control for people with diabetes

| Biochemical index | Fasting glucose | Bedtime glucose (mg/dl) | $HbA_{1c}$ (%) |
|---|---|---|---|
| Nondiabetic | <115 | <120 | <6 |
| Goal | 80–120 | 100–140 | <7 |
| Action suggested | >140 | >160 | >8 |

Insulin resistance is an essential feature of a great variety of clinical disorders, such as diabetes mellitus, obesity and certain types of hypertension. Individuals with non-insulin dependent diabetes present with insulin resistance in peripheral tissues. They have a subnormal glucose utilization in skeletal muscle, where glucose transport across the cell membrane of skeletal muscle is the rate limiting step in glucose metabolism. It is possible that a defect exists in insulin-dependent glucose transport in skeletal muscle in diabetic states, where decreased levels of the glucose transporter 4 protein (GLUT4) have been observed. In adipose and muscle cells, insulin stimulates a rapid and dramatic increase in glucose uptake, primarily by promoting the redistribution of the GLUT4 glucose transporter from its intracellular storage site to the plasma membrane. Impaired glucose tolerance (IGT) is associated with a normal fasting blood glucose but an elevated postprandial blood sugar between 7.8 and 11 mmol/L (140 and 199 mg/dL). Some patients with IGT are hyperinsulinimic, and 30 percent progress to NIDDM.

Clinically, metformin lowers fasting and postprandial hyperglycemia. The decrease in fasting plasma glucose is approximately 25–30%. Unlike oral sulfonylureas, metformin rarely causes hypoglycemia. Thus, metformin demonstrates more of an antihyperglycemic action than a hypoglycemic action. Metformin does not cause weight gain and in fact, may cause a modest weight loss due to drug-induced anorexia. Metformin also decreases plasma VLDL triglycerides. Patients receiving metformin show a significant improvement in hemoglobin A1c, and a tendency toward improvement in the lipid profile, especially when baseline values are abnormally elevated.

The subject complexes are administered to obese patients for purposes of appetite suppression. Human obesity is a widespread and serious disorder, affecting a high percentage of the adult population in developed countries. In spite of an association with heart disease, type II diabetes, cancer, and other conditions, few persons are able to permanently achieve significant weight loss. Patients may use various criteria for determining obesity. Conveniently, a body mass index (BMI) is calculated, where a person having a BMI of greater than 25 is overweight and may considered for treatment with the subject vanadium biguanide complex formulations.

Hypertension and diabetes mellitus are interrelated diseases, which, if untreated, strongly predispose to atherosclerotic cardiovascular disease. Lifestyle and genetic factors are important in the genesis of both conditions. An estimated 3 million Americans have both diabetes and hypertension. Hypertension is approximately twice as common in persons with diabetes as in those without. The prevalence of hypertension and type II diabetes, or non-insulin-dependent diabetes mellitus (NIDDM), increases with age.

Hypertension should not be diagnosed on the basis of a single measurement. Initial elevated readings should be confirmed on at least two subsequent visits over 1 week or more with average diastolic blood pressure of 90 mmHg or greater or systolic blood pressure of 140 mmHg or greater required for diagnosis of hypertension. Special care is warranted in diagnosing hypertension in persons with diabetes because of greater variability of blood pressure and a much greater likelihood of isolated systolic hypertension. A goal blood pressure of less than 130/85 mmHg is recommended for these patients.

Alterations in circulating lipids are also commonly associated with diabetes and hyperglycemia. Persons with type II diabetes and impaired glucose tolerance experience twice the incidence of hypertriglyceridemia and low high density lipoprotein (HDL) cholesterol of persons who do not have diabetes. These changes are thought to be related to insulin resistance and hyperinsulinemia. Low density lipoprotein (LDL) cholesterol in diabetes is more prone to glycation and oxidation. These biochemical changes increase the atherogenicity and decrease the metabolism of LDL cholesterol.

It is to be understood that this invention is not limited to the particular methodology, protocols, formulations and reagents described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a complex" includes a plurality of such complexes and reference to "the formulation" includes reference to one or more formulations and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

EXAMPLE 1

Preparation and Characterization of Oxovanadium(IV)-Biguanide Complexes

A class of compounds that shows anti-diabetic behavior without altering insulin secretion is the biguanides. These are very strong diacid bases characterized by strongly basic primary dissociation constants and considerably weaker secondary ones. They have a conjugated double bond system stabilized as a hydrogen-bonded intermolecular six-membered ring. Amongst this class are metformin ($N^1,N^1$-dimethylbiguanide hydrochloride) and phenformin (phenethylbiguanide hydrochloride)—synthetic oral glucose-lowering agents introduced in the 1950's to treat NIDDM. However, the latter has been withdrawn due to serious lactic acidosis side effects. Metformin, having fewer side effects, is used world-wide in monotherapy and combination treatment with sulphonylureas.

Biguanide and substituted biguanides (shown as bases)

|  | $R_1$ | $R_2$ |
|---|---|---|
| Hbig = biguanide | H | H |
| Hphen = phenformin | H | $CH_2CH_2C_6H_5$ |
| Hmet = metformin | $CH_3$ | $CH_3$ |

Bidentate biguanide and substituted biguanide ligands form brilliantly colorful, stable metal and non-metal chelate compounds with extensive π delocalization. Complex compounds of biguanides with various transition metals such as Cu(II), Ni(II), Co(II), Co(III), Cr(III), Mn(IIII), Mn(IV), V(IV), Re(V), Os(VI), Ag(III), Pd(II), and Zn have been cited by Ray (1961), supra., but with little characterization and no reaction chemistry. The idea of combining vanadium and biguanide to form potential synergistic compounds effective in diabetes treatment is particularly attractive. The preparation and characterization of oxovanadium(IV) combined with each of biguanide, metformin, and phenformin (VO(big)$_2$, VO(met)$_2$, and VO(phen)$_2$, respectively) are discussed here. Rat studies with VO(met)$_2$ show that the complex is active in lowering plasma glucose.

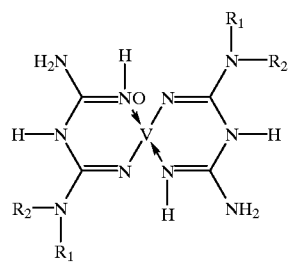

$VOL_2$ complexes prepared, where the ligands are metformin, phenformic and biguanide.

Materials

Dicyandiamide, metformin, β-phenethylamine hydrochloride, and vanadyl sulfate trihydrate were purchased from Sigma/Aldrich and used without further purification. Biguanide and phenformin were prepared following literature procedures by combining dicyandiamide with ammonium chloride (Karipides et al. (1963) *Inorg. Syn.* VII:56) and phenethylamine hydrochloride (Shapiro et al. (1959) *J. Am. Chem. Soc.* 81:2220) respectively. All complex reactions were carried out under argon. Water was deionized (Barnstead D8902 and D8904 cartridges) and distilled (Corning MP-1 Megapore Still) before use. Chemicals and solvents used were reagent grade (Fisher, Aldrich) and used without further purification unless otherwise specified.

Instrumentation

Infrared spectra were recorded as KBr disks in the range 4000–400 cm$^{-1}$ on a Galaxy Series 5000 spectrometer. Mass spectra (+ion) were obtained with a Kratos MS 50 (electron-impact ionization, EI), or a Kratos Concept II H32Q (Cs+ liquid secondary ion mass spectrometry, LSIMS) instrument. Melting points were measured on a Mel-Temp apparatus and are uncorrected. All C, H, N analyses were performed on a Carlo Erba instrument in this department. Room temperature (293 K) magnetic susceptibility measurements were obtained with a Johnson Matthey magnetic susceptibility balance, using Hg[Co(NCS)$_4$] as the standard.

Preparation of Ligands

Biguanide sulfate, $C_2H_7N_5.H_2SO_4$,(Hbig.H$_2$SO$_4$).

Biguanide acid sulfate was prepared by the ammoniation of dicyandiamide (5 g, 0.059 mol) with ammonium chloride (8 g, 0.150 mol). The yield obtained was 1.12 g (9.5%) after drying at 100° C. for 12 hours; m.p. 231–232° C. Anal. Calcd (found) for $C_2H_7N_5.H_2SO_4$: C, 12.06 (12.09); H, 4.55 (4.51); N, 35.16 (35.17).

Phenformin, $C_{10}H_{15}N_5.HCl$, (Hphen.HCl). β-phenethylamine hydrochloride (10 g, 0.0633 mol) and dicyandiamide (5.31 g, 0.0632 mol) were heated in an oil bath up to 130° C. gradually with stirring. The mixture was further heated for an hour at 145–150° C. When cool, the product was recrystallized from isopropanol to obtain a yield of 7.22 g (47%); m.p. 175–178° C. Anal. Calcd (found) for $C_{10}H_{15}N_5.HCl$: C, 49.69 (50.24); H, 6.67 (6.76); N, 28.97 (28.02).

Preparation of Complexes

Bis(biguanidato)oxovanadium(IV), VO(big)$_2$.1.5H$_2$O

Biguanide sulfate (0.46 g, 2.31 mmol) was dissolved in 5 mL hot water. Aqueous VOSO$_4$.3H$_2$O (0.25 g, 1.15 mmol) was added to yield a clear blue solution. Dilute NaOH (0.28 g, 7 mmol) was added dropwise and slowly, turning the solution gray, then light brown, and finally green (pH ~11). The mixture was stirred for 1 hour and the green precipitate was filtered under vacuum, washed with water followed by ethyl ether, and dried overnight in vacuo. The yield was 0.25 g (81%). IR (cm$^{-1}$, KBr disk) 942 ($v_{V=O}$); +LSIMS m/z= 268 ([M+1]$^+$, [C$_4$H$_{13}$N$_{10}$OV]$^+$). The solid state magnetic moment was 1.81 $\mu_B$. Anal. Calcd (found) for C$_4$H$_{12}$N$_{10}$OV.1.5H$_2$O: C, 16.33 (16.52); H, 5.14 (4.81); N, 47.61 (47.15).

Bis(N$^1$,N$^1$-dimethylbiguanidato)oxovanadium(IV), VO(met)$_2$.H$_2$O

VOSO$_4$.3H$_2$O (1 g, 4.6 mmol) was dissolved in 5 mL water and added slowly to an aqueous solution of 2 equivalents metformin (1.52 g, 9.2 mmol). Dilute NaOH (0.9 g, 23 mmol) was added dropwise to bring the pH to ~12. Initial addition of base resulted in brown hydroxide complex formation; however, upon complete addition, light green solid precipitated. The solution was stirred for 2–3 hours and the solid was collected by vacuum filtration, washed with cold water followed by ether, and dried overnight in vacuo. The yield was 0.9 g (56%). IR (cm$^{-1}$, KBr disk) 929 ($v_{V=O}$); EIMS m/z=323 (M$^+$, [C$_8$H$_{20}$N$_{10}$OV]$^+$). The solid state magnetic moment was 1.94 $\mu_B$. Anal. Calcd (found) for C$_8$H$_{20}$N$_{10}$OV.H$_2$O: C, 28.16 (28.44); H, 6.50 (6.59); N, 41.04 (41.26).

Bis(phenethylbiguanidato)oxovanadium(IV), VO(phen)$_2$.H$_2$O

VOSO$_4$.3H$_2$O (0.45 g, 2.07 mmol) was dissolved in ~3 mL water and added slowly to an aqueous solution of 2 equivalents phenformin (1 g, 4.14 mmol). Dilute NaOH (0.166 g, 4.14 mmol) was added dropwise to bring the pH to ~12. Initial addition of base resulted in light brown hydroxide complex formation; however, upon complete addition and after stirring for 1 hour, a light blue solid precipitated. The solution was stirred for an additional hour and the solid was collected by vacuum filtration, washed with cold water followed by ether, and dried overnight in vacuo. The yield was 0.72 g (37%). IR (cm$^{-1}$, KBr disk) 953 ($v_{V=O}$); +LSIMS m/z=476 ([M+1]$^+$, [C$_{20}$H$_{29}$N$_{10}$OV]$^+$). Anal. Calcd (found) for C$_{20}$H$_{28}$N$_{10}$OV.H$_2$O: C, 48.68 (48.64); H, 6.13 (5.80); N, 28.38 (26.59).

Results

VOL$_2$

The oxovanadium(IV)-biguanide complexes are easily prepared by the addition of vanadyl sulfate to alkaline aqueous solutions of each biguanide with varying yields. The resultant products are highly colored, air stable powders. However, the three complexes are not soluble in common organic solvents such as alcohol, chloroform, methylene chloride, THF, acetonitrile, and acetone, hence they could not be recrystallized. In water, hydrolysis occurs and a brown solution results. In DMSO, each complex turns purple and ultimately dissolves. Infrared spectra show the sulfoxide stretching resulting from solvation. Green VO(big)$_2$ and VO(met)$_2$ are initially recovered by the addition of water. From the solvated species, oxidation to V(V) (yellow solution) occurs when methanol is added, however, this has not been isolated. The compounds are decomposed by acids.

Stretching frequencies of the V=O bond in oxovanadium complexes occur in the region of 930 to 1030 cm$^{-1}$. The complexes VO(big)$_2$, VO(met)$_2$, and VO(phen)$_2$ have low $v_{V=O}$ due to the presence of strong out-of-plane d$_\pi$-p$_\pi$ bonding. Room temperature magnetic moments are close to the spin-only value of 1.73, predicted for the d$^1$ system of V(IV) with one unpaired electron. Literature values of 1.48–1.62 BM (Ray (1961) Chem. Rev. 61:313) for some vanadyl biguanide compounds are lower possibly from an exchange interaction leading to the formation of a metal-metal bond.

Vanadium(IV) forms stable complexes with various ligands, most favorably with O and N coordination. Generally, bivalent metals combine with two molecules of biguanide to form 4-coordinated planar complexes, while trivalent metals combine with three molecules of ligand to yield a 6-coordinated octahedral arrangement, as shown by the crystal structures of Cr(big)$_3$ (Coghi et al. (1976) Acta. Cryst. B32:842) and Mn(big)$_3$ (Hart et al. (1992) J. Chem. Soc. Chem. Commun. 894). Vanadyl complexes typically have a square pyramidal geometry, which is postulated for these three prepared complexes with biguanides. Two mono-deprotonated biguanides coordinate through the nitrogens to form two stable 6-membered chelate rings bound to vanadium, affording lipophilic bis(ligand) metal complexes of neutral charge.

The solution equilibria and stability data of the vanadyl-biguanide system could not be determined as hydrolysis predominates at approximately pH 4.

Crystals of either complex could not be obtained due to their limited solubility. A structure similar to that of bis (ligand)oxovanadium(IV) complexes (e.g. BMOV[11]) is expected—a simple square pyramidal configuration with two biguanidato ligands in a trans arrangement around the base of the square pyramid and the V=O unit axial. V=O distances of 1.5–1.6 Å are common.

EXAMPLE 2

Effect of VO(met)$_2$ on STZ-Diabetic Rats

Use of 1,1-dimethylbiguanide-vanadium Complexes in the Treatment of Hyperglycemia Nineteen male Wistar rats weighing 190–220 g were obtained from the Animal Care Center at the University of British Columbia. Animals were acclimatized for a period of 7–14 days in our facility.

Animals were made diabetic with a single intravenous injection of streptozotocin (STZ) (Source: Sigma) at 60 mg/kg in 0.9% NaCl (1 mL/kg volume) (Source: BDH) under light halothane (Halocarbon Laboratories) anaesthesia. The diabetic state was confirmed on the third day post-stz-administration with Ames brand Glucometer and Glucostix reading, and blood glucose levels of over 13 mM were categorized as diabetic. All of the animals qualified.

On day seven post STZ-administration, the nineteen animals were divided randomly into four groups. These four groups received one of four treatments, including control. The control group received an equivalent volume of 3% gum Arabic carrier alone. The other three treatment groups were: Bis(ethylmaltolato) oxovanadium(IV)("BEOV"), 1,1-dimethylbiguanide ("metformin"), and vanadium(IV)-metformin complex (B(met)OV). The metformin was manufactured by Sigma.

The gum arabic was prepared by dissolving 3 g of gum arabic in 100 mL of distilled water. This mixture was sealed and stored under refrigeration for 1 week before the experiment.

All drugs were injected intraperitoneally into the rats at a volume of 5 ml/kg in 3% gum Arabic. The dose of administration was 0.12 mmol/kg.

Animals were allowed free access to food.

Blood was collected from the tail into heparinized capillary tubes and centrifuged at 10,000 g for 15 minutes. Blood was collected in 50 $\mu$L aliquots in this manner prior to drug administration, and at 2, 4, 6, 8, 12, 16, 20, 24, 48 and 72 hours post administration.

The plasma was analyzed for glucose levels using Boehringer Mannheim Glucose Kits (glucose oxidase method).

| Time of blood sample | Pre treat | 2 h | 4 h | 6 h | 8 h | 12 h | 16 h | 20 h | 24 h | 48 h | 72 | AUC mmol/L/h |
|---|---|---|---|---|---|---|---|---|---|---|---|---|
| Test compound/# animals | | | | | | | | | | | | |
| gum Arabic control (4) | 21.85 | 21.22 | 21.02 | 20.28 | 20.79 | 22.70 | 22.78 | 23.29 | 20.89 | 22.18 | 21.98 | 1606.91 |
| BEOV (5) | 22.03 | 21.01 | 19.04 | 18.20 | 17.89 | 18.18 | 17.57 | 17.02 | 15.95 | 15.90 | 15.27 | 1197.30 |
| Metformin (5) | 21.58 | 21.11 | 19.33 | 19.03 | 19.10 | 23.40 | 23.55 | 23.27 | 22.24 | 21.28 | 21.41 | 1572.94 |
| Vanadium-metformin (5) | 22.21 | 20.55 | 17.95 | 17.67 | 17.79 | 20.37 | 19.46 | 19.58 | 16.76 | 18.33 | 18.66 | 1362.61 |

Blood Glucose Levels Measured by Glucose Oxidase method: Average of all animals in each group-Millimoles · hr per Liter Conclusion: IP injection of 0.12 mmol/kg metformin in 3% gum Arabic or 3% gum Arabic alone did not acutely lower plasma glucose levels in STZ diabetic rats over 72 hours. Both BEOV and B(met)OV reduced plasma glucose levels to <9 mmol/L in 40% of STX-diabetic rats.

What is claimed is:

1. A pharmaceutical composition comprising:

a vanadium biguanide complex of the formula:

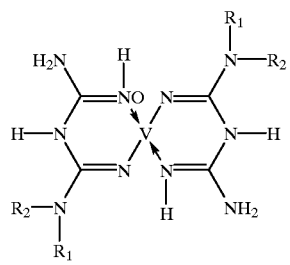

where $R_1$ and $R_2$ are, independently selected from the group consisting of H, methyl, ethyl, propyl, isopropyl, butyl, cycloalkyls, phenyl and phenethyl; and a pharmaceutically acceptable carrier, wherein the amount of said vanadium biguanide complex provides an effective dose for the treatment of elevated blood sugar.

2. The pharmaceutical composition of claim 1, wherein said biguanide is 1,1-dimethylbiguanide.

3. The pharmaceutical composition of claim 1, wherein said biguanide is 1-phenethylbiguanide.

4. The pharmaceutical composition of claim 1, wherein said biguanide 1-butylbiguanide.

5. The pharmaceutical composition of claim 1 wherein said vanadium is present as V(IV).

6. The pharmaceutical composition of claim 1, wherein said vanadium is present as V(V).

7. A pharmaceutical composition comprising:

a vanadium biguanide complex of the formula:

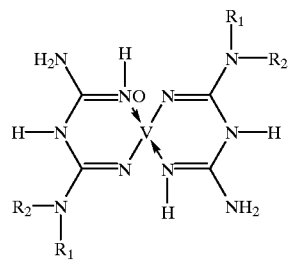

where $R_1$ and $R_2$ are, independently selected from the group consisting of H, methyl, ethyl, propyl, isopropyl, butyl, cycloalkyls, phenyl and phenethyl; and a pharmaceutically acceptable carrier, wherein the amount of said vanadium biguanide complex provides an effective dose for the treatment of elevated blood sugar, and wherein said composition is formulated for oral administration.

8. A pharmaceutical composition comprising:

a vanadium biguanide complex of the formula:

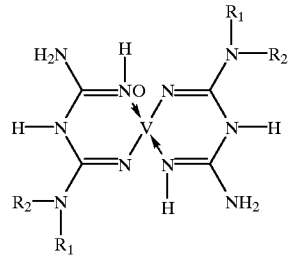

where $R_1$ and $R_2$ are, independently selected from the group consisting of H, methyl, ethyl, propyl, isopropyl, butyl, cycloalkyls, phenyl and phenethyl; and a pharmaceutically acceptable carrier, wherein the amount of said vanadium biguanide complex provides an effective dose for the treatment of elevated blood sugar, and a second pharmacological agent effective in treating hyperglycemia.

9. The pharmaceutical composition of claim 8, wherein said second pharmacological agent is insulin.

10. The pharmaceutical composition of claim 8, wherein said second pharmacological agent is a benzenesulfonylurea derivatives of the type $R_4C_6H_4SO_2NHCONHR_5$.

* * * * *

UNITED STATES PATENT AND TRADEMARK OFFICE
CERTIFICATE OF CORRECTION

PATENT NO. : 6,287,586 B1
DATED : September 11, 2001
INVENTOR(S) : Orvig et al.

It is certified that error appears in the above-identified patent and that said Letters Patent is hereby corrected as shown below:

<u>Columns 3, 10 and claims 1, 7 and 8,</u>
Please replace the chemical structure found in columns three and ten and in claims one, seven and eight with the correct chemical structure provided below:

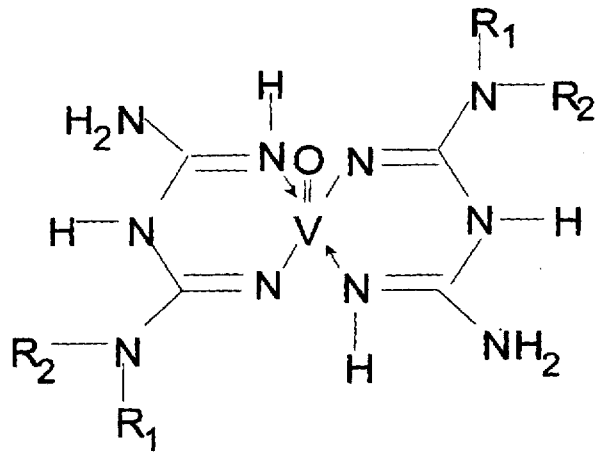

Signed and Sealed this

Sixteenth Day of April, 2002

Attest:

JAMES E. ROGAN
*Attesting Officer*   *Director of the United States Patent and Trademark Office*